(12) United States Patent
Nozaki et al.

(10) Patent No.: US 6,887,204 B2
(45) Date of Patent: May 3, 2005

(54) CONNECTOR CASE, ULTRASONIC PROBE AND ULTRASONIC IMAGING APPARATUS

(75) Inventors: Mitsuhiro Nozaki, Tokyo (JP); Masami Uchibori, Tokyo (JP); Sotaro Kawae, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 239 days.

(21) Appl. No.: 10/121,906

(22) Filed: Apr. 12, 2002

(65) Prior Publication Data

US 2002/0151791 A1 Oct. 17, 2002

(30) Foreign Application Priority Data

Apr. 17, 2001 (JP) .................................. 2001-118165

(51) Int. Cl.[7] .................................................. A61B 8/14
(52) U.S. Cl. ...................................................... 600/459
(58) Field of Search ............................... 600/407–472; 73/625–633; 367/7, 11, 130, 138; 128/916; 310/330–334; 439/608, 638, 676, 680, 578; 29/25.35; 348/65

(56) References Cited

U.S. PATENT DOCUMENTS

| 4,242,778 A | 1/1981 | Kay |
| 4,925,309 A | 5/1990 | Endo et al. |

FOREIGN PATENT DOCUMENTS

| GB | 755385 | 8/1956 |
| JP | 200200654 | 7/2000 |

OTHER PUBLICATIONS

International Search Report, dated Nov. 4, 2003, Application No. FR 0204770, 3 pgs.

*Primary Examiner*—Ali Imam
(74) *Attorney, Agent, or Firm*—Carl B. Horton, Esq.; Armstrong Teasdale LLP (57) ABSTRACT

In order to facilitate recognition of the correct orientation of a connector, the rear portion of a connector 24 is configured to form an elevation angle when the front portion of the connector can be correctly inserted into a receptacle 500 in a horizontal direction.

21 Claims, 7 Drawing Sheets

CONNECTOR CASE, ULTRASONIC PROBE AND ULTRASONIC IMAGING APPARATUS

CROSS REFERENCE TO RELATED APPLICATIONS

This application claims the benefit of Japanese Application No. 2001-118165 filed Apr. 17, 2001.

BACKGROUND OF THE INVENTION

The present invention relates to a connector case, ultrasonic probe and ultrasonic imaging apparatus, and particularly to a connector case containing an electric contact assembly, an ultrasonic probe comprising such a connector case, and an ultrasonic imaging apparatus comprising such an ultrasonic probe.

An ultrasonic imaging apparatus scans the interior of a subject to be imaged with a beam of pulsed ultrasound, receives an echo, calculates image data corresponding to the intensity of the echo, and produces an image commonly referred to as a B-mode image based on the image data. This process is sometimes referred to as B-mode imaging.

Moreover, the ultrasonic imaging apparatus calculates a Doppler shift of the echo of pulsed ultrasound, and produces a color image representing dynamics of blood flow etc., which is commonly referred to as a color Doppler image, based on the Doppler shift. This process is sometimes referred to as color Doppler imaging.

Furthermore, the ultrasonic imaging apparatus obtains a Doppler signal of an echo of continuous wave (CW) ultrasound, and displays the signal as a frequency spectral image and as a sound (Doppler sound). This process is sometimes referred to as continuous wave Doppler measurement.

In any of the above-described imaging or measurement, an ultrasonic probe is used for transmission of the ultrasound and reception of the echo. The ultrasonic probe is connected to a body of the imaging apparatus via a flexible cable. A user takes the ultrasonic probe in the hand, and uses the probe by abutting it against a desired portion on the subject to be imaged.

A plurality of types of purpose-specific ultrasonic probes are kept handy, and an appropriate one of them is selected for the purpose at hand and used by connecting the probe to the imaging apparatus body. The connection of the ultrasonic probe with the imaging apparatus body is established by a connector. The user connects the ultrasonic probe to the imaging apparatus body by inserting the connector provided at an end of the cable of the ultrasonic probe into a receptacle provided in the imaging apparatus body; and removes the ultrasonic probe from the imaging apparatus body by withdrawing the connector from the receptacle.

The orientation of the connector in which the connector can be inserted into the receptacle is fixed and the connector has a structure such that it cannot be inserted in orientations other than the fixed one. However, the user may, by mistake for example, sometimes attempt to insert the connector forcibly in a wrong orientation and break the connector or receptacle.

SUMMARY OF THE INVENTION

It is therefore an object of the present invention to provide a connector case that facilitates recognition of the correct orientation of a connector, an ultrasonic probe comprising such a connector case, and an ultrasonic imaging apparatus comprising such an ultrasonic probe.

(1) The present invention, in one aspect for achieving the aforementioned object, is a connector case having a front portion to be inserted into a receptacle and a rear portion out of which a cable is led, and containing an electric contact assembly therein, wherein the connector case is configured so that the rear portion forms an elevation angle when the front portion can be correctly inserted into the receptacle in a horizontal direction.

(2) The present invention, in another aspect for achieving the aforementioned object, is an ultrasonic probe comprising: a probe body; a cable having one end connected to the probe body; an electric contact assembly connected to the other end of the cable; and a connector case having a front portion to be inserted into a receptacle and a rear portion out of which the cable is led, and containing the electric contact assembly therein, the connector case being configured so that the rear portion forms an elevation angle when the front portion can be correctly inserted into the receptacle in a horizontal direction.

(3) The present invention, in still another aspect for achieving the aforementioned object, is an ultrasonic imaging apparatus comprising: an imaging apparatus body provided with a receptacle; a probe body; a cable having one end connected to the probe body; an electric contact assembly connected to the other end of the cable; and a connector case having a front portion to be inserted into the receptacle and a rear portion out of which the cable is led, and containing the electric contact assembly therein, the connector case being configured so that the rear portion forms an elevation angle when the front portion can be correctly inserted into the receptacle in a horizontal direction.

In the invention of the aspects as described in (1)–(3), the connector case is configured so that the rear portion forms an elevation angle when the front portion can be correctly inserted into the receptacle in a horizontal direction; therefore, when the user attempts to insert the front portion inversely, the rear portion is directed downward to awkwardly interfere with the supporting surface on which the apparatus provided with the receptacle is placed. Thus, the user becomes aware of the mistake instantaneously.

(4) The present invention, in still another aspect for achieving the aforementioned object, is a connector case having a front portion to be inserted into a receptacle and a rear portion out of which a cable is led, and containing an electric contact assembly therein, wherein the connector case has a color on a side that is obverse when the front portion can be correctly inserted into the receptacle in a horizontal direction, which color is different from that on a reverse side.

(5) The present invention, in still another aspect for achieving the aforementioned object, is an ultrasonic probe comprising: a probe body; a cable having one end connected to the probe body; an electric contact assembly connected to the other end of the cable; and a connector case having a front portion to be inserted into a receptacle and a rear portion out of which the cable is led, and containing the electric contact assembly therein, the connector case having a color on a side that is obverse when the front portion can be correctly inserted into the receptacle in a horizontal direction, which color is different from that on a reverse side.

(6) The present invention, in still another aspect for achieving the aforementioned object, is an ultrasonic imaging apparatus comprising: an imaging apparatus body provided with a receptacle; a probe body; a cable having one end connected to the probe body; an electric contact assembly connected to the other end of the cable; and a connector case having a front portion to be inserted into the receptacle and a rear portion out of which the cable is led, and containing the electric contact assembly therein, the connector case having a color on a side that is obverse when the front portion can be correctly inserted into the receptacle in a horizontal direction, which color is different from that on a reverse side.

In the invention of the aspects as described in (4)–(6), the connector case is configured to have a color on a side that is obverse when the front portion can be correctly inserted into the receptacle in a horizontal direction, which color is different from that on a reverse side; therefore, when the user attempts to insert the front portion inversely, the user is made instantaneously aware of the mistake by the different color.

(7) The present invention, in still another aspect for achieving the aforementioned object, is a connector case having a front portion to be inserted into a receptacle and a rear portion out of which a cable is led, and containing an electric contact assembly therein, wherein the connector case comprises an insertion stopping member that is retracted from an insertion stopping position to a release position by gravity when the front portion is in a position in which it can be correctly inserted into the receptacle in a horizontal direction.

(8) The present invention, in still another aspect for achieving the aforementioned object, is an ultrasonic probe comprising: a probe body; a cable having one end connected to the probe body; an electric contact assembly connected to the other end of the cable; and a connector case having a front portion to be inserted into a receptacle and a rear portion out of which the cable is led, and containing the electric contact assembly therein, the connector case comprising an insertion stopping member that is retracted from an insertion stopping position to a release position by gravity when the front portion is in a position in which it can be correctly inserted into the receptacle in a horizontal direction.

(9) The present invention, in still another aspect for achieving the aforementioned object, is an ultrasonic imaging apparatus comprising: an imaging apparatus body provided with a receptacle; a probe body; a cable having one end connected to the probe body; an electric contact assembly connected to the other end of the cable; and a connector case having a front portion to be inserted into the receptacle and a rear portion out of which the cable is led, and containing the electric contact assembly therein, the connector case comprising an insertion stopping member that is retracted from an insertion stopping position to a release position by gravity when the front portion is in a position in which it can be correctly inserted into the receptacle in a horizontal direction.

In the invention of the aspects as described in (7)–(9), the connector case is configured to have an insertion stopping member that is retracted from an insertion stopping position to a release position by gravity when the front portion is in a position in which it can be correctly inserted into the receptacle in a horizontal direction; therefore, even if the user attempts to insert the front portion inversely, the insertion is stopped by the insertion stopping member and the user becomes aware of the mistake instantaneously.

Preferably, the insertion stopping member has a pivotally supported arm, one end of which is provided with a stopper plate and the other end of which is provided with a weight, so that the configuration can be simplified.

(10) The present invention, in still another aspect for achieving the aforementioned object, is an ultrasonic imaging apparatus comprising: an imaging apparatus body provided with a receptacle; a probe body; a cable having one end connected to the probe body; a connector case having a front portion to be inserted into the receptacle and a rear portion out of which the cable is led, and containing an electric contact assembly connected to the other end of the cable therein; and warning means for generating a warning sound when the front portion of the connector case is about to be inserted into the receptacle in an incorrect orientation.

In the invention as described in (10), there is provided warning means for generating a warning sound when the front portion of the connector case is about to be inserted into the receptacle in an incorrect orientation; therefore, when the user attempts to insert the front portion inversely, the user is made instantaneously aware of the mistake by the warning sound.

Preferably, the sound is a noise, because the warning means can be simplified.

Preferably, the sound is a voice message, because an explicit warning can be made.

In this case, the voice message is preferably a multilingual voice message, because a variety of users can be accommodated.

Preferably, the imaging apparatus body has a generally rectangular-parallelepiped outer shape in which the height dimension is smaller than the length and width dimensions, and has a housing provided with the receptacle on one of its surfaces other than the bottom and upper surfaces, so that a flat ultrasonic imaging apparatus can be constructed.

In this case, the imaging apparatus body preferably has on an upper surface of the housing a generally planar display section that is tiltable around a hinge, so that a flat ultrasonic imaging apparatus including the display section can be constructed.

As described above in detail, the present invention can provide a connector case that facilitates recognition of the correct orientation of a connector, an ultrasonic probe comprising such a connector case, and an ultrasonic imaging apparatus comprising such an ultrasonic probe.

Further objects and advantages of the present invention will be apparent from the following description of the preferred embodiments of the invention as illustrated in the accompanying drawings.

DETAILED DESCRIPTION OF THE INVENTION

Figure 1:
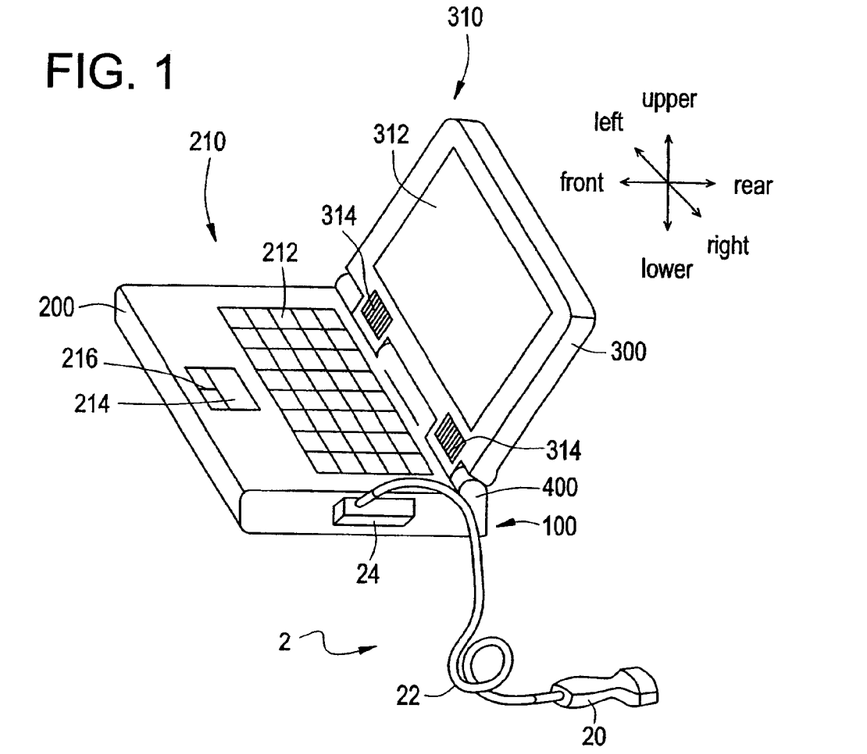
FIG. 1 is a schematic view showing the physical configuration of an apparatus in accordance with an embodiment of the present invention.

Several embodiments of the present invention will now be described in detail with reference to the accompanying drawings. It should be noted that the present invention is not limited to the embodiments. The physical configuration of an ultrasonic imaging apparatus is schematically shown in FIG. 1, which is one embodiment of the present invention. The configuration of the apparatus represents an embodiment of the apparatus in accordance with the present invention. With respect to the apparatus, front and rear, right and left, and up and down directions are defined as indicated by arrows shown in FIG. 1.

As shown in FIG. 1, the present apparatus has an imaging apparatus body 100 and an ultrasonic probe 2. The ultrasonic probe 2 is comprised of a probe body 20, a cable 22 and a connector 24. The probe body 20 is connected to one end of the cable 22, and is removably connected to the imaging apparatus body 100 via the connector 24 provided at the other end of the cable 22.

Figure 2:
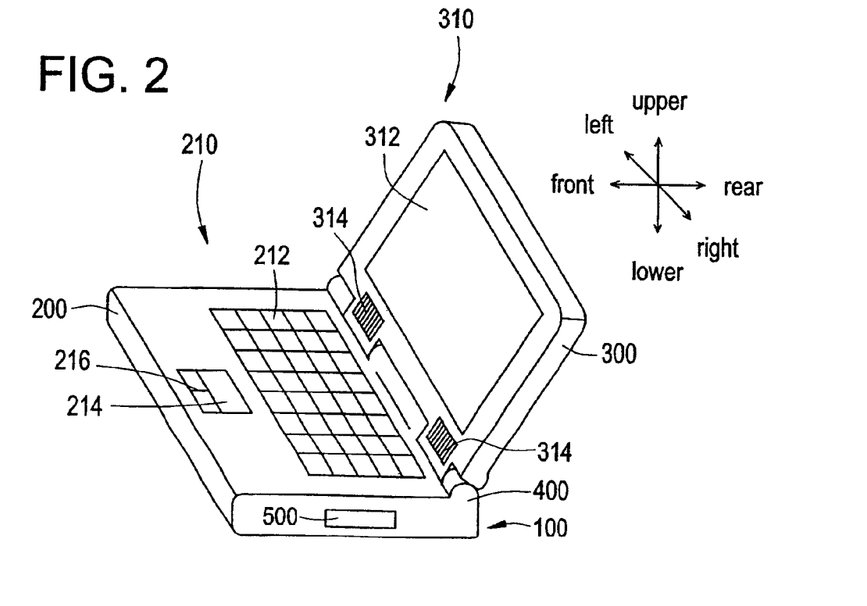
FIGS. 2 and 3 are schematic views showing the physical configuration of an imaging apparatus body.

FIG. 2 shows the imaging apparatus body 100 without the ultrasonic probe 2. As shown, the imaging apparatus body 100 is constructed by joining a generally planar panel 300 to a generally box-shaped body 200 via a hinge 400. The hinge 400 is provided between the upper portion of the rear end of the body 200 and the lower end portion of the panel 300.

The panel 300 can rotate relative to the body 200 around the hinge 400. The hinge 400 has a moderate frictional resistance to allow the panel 300 to be fixed at an arbitrary rotation angle.

Figure 3:
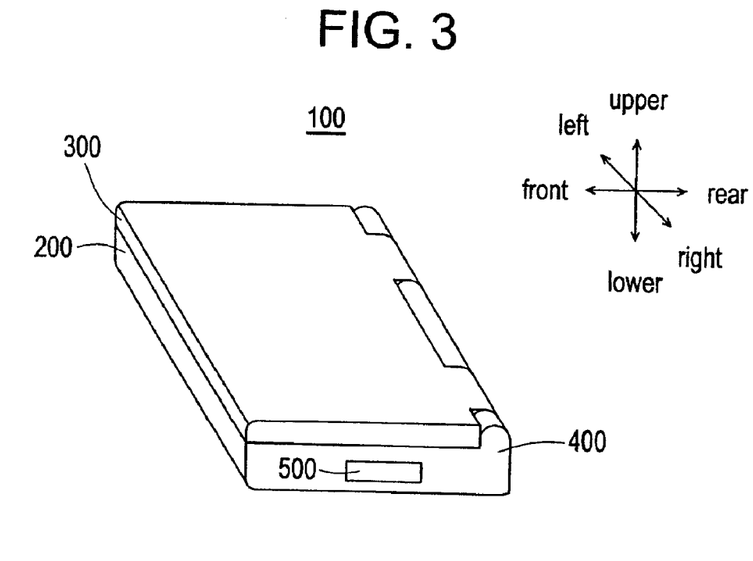

When the panel 300 is rotated counterclockwise to the maximum degree in the drawing, the panel 300 can be turned down on the upper surface of the body 200 as shown in FIG. 3. This condition will be sometimes referred to as the folded condition of the imaging apparatus body 100 hereinbelow. That is, the panel 300 can tilt toward the body 200. In the folded condition, the imaging apparatus body 100 has a so-called slim and generally rectangular-parallelepiped outer shape in which the top-bottom dimension is smaller than the front-rear dimension and the right-left dimension.

The upper surface of the body 200 is configured as an operating section 210 of the present apparatus. The operating section 210 has a keyboard 212 and an input pad 214. The input pad 214 is provided with a pair of click buttons 216. The input pad 214 is used as a pointing device.

A right side surface of the body 200 is provided with a receptacle 500 for connecting the connector 24 of the ultrasonic probe 2. It should be noted that the position at which the receptacle 500 is disposed is not limited to the right side surface, but the receptacle 500 may be provided on the left side, rear or front surfaces; in effect, the position may be any surface other than the upper and bottom surfaces. The receptacle 500 is an embodiment of the receptacle of the present invention.

A front surface of the panel 300 is configured as a display section 310. The display section 310 has an image display device 312 and a pair of sound output devices 314. For the image display device 312, a flat panel display, such as, for example, an LCD (liquid crystal display), is employed. For the sound output devices 314, speakers, for example, are employed.

Figure 4:
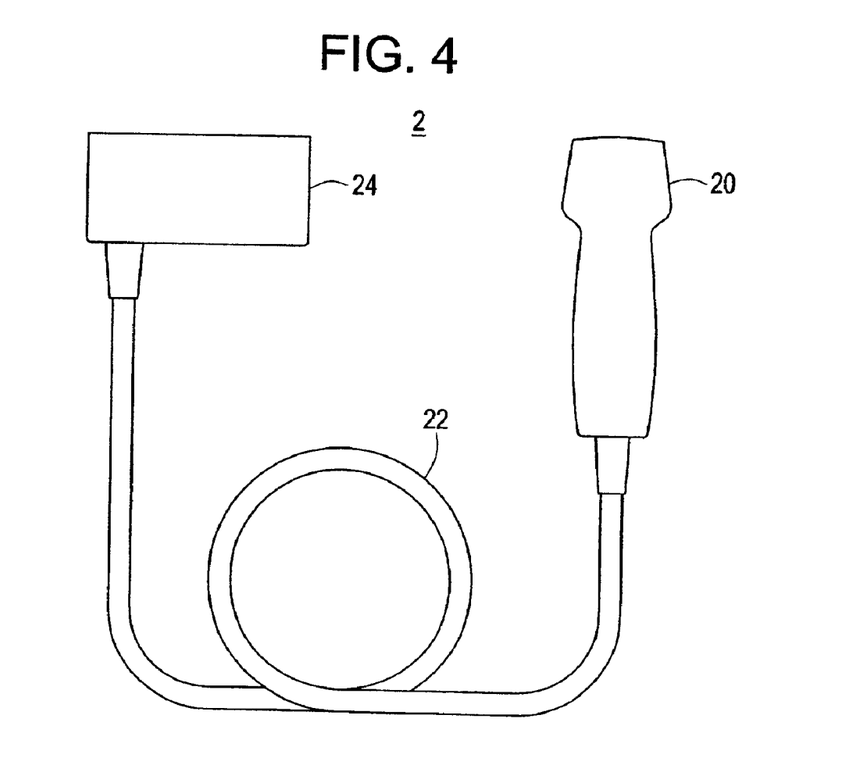
FIG. 4 is a schematic view showing the physical configuration of an ultrasonic probe.

FIG. 4 shows the ultrasonic probe 2 removed from the imaging apparatus body 100. The ultrasonic probe 2 is an embodiment of the ultrasonic probe of the present invention. The configuration of the probe represents an embodiment of the ultrasonic probe in accordance with the present invention.

The probe body 20 is connected with one end of the cable 22, and the other end of the cable 22 is connected with the connector 24. The probe body 20 is an embodiment of the probe body of the present invention. The cable 22 is an embodiment of the cable of the present invention.

Figure 5A:
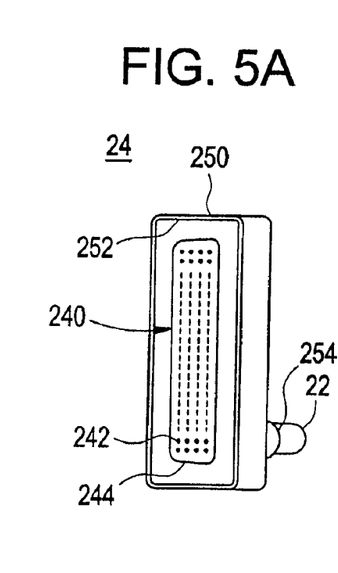
FIG. 5 is the configuration of a connector.
Figure 5B:
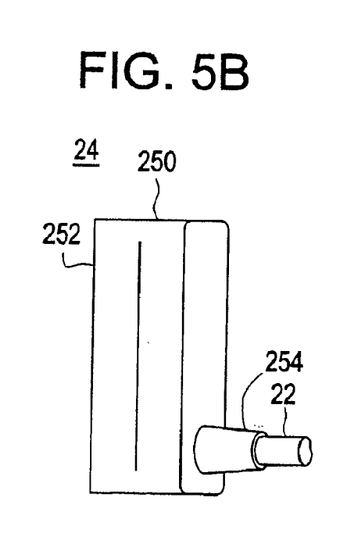
Figure 5C:
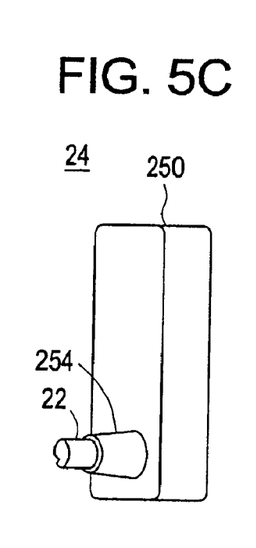
Figure 5D:
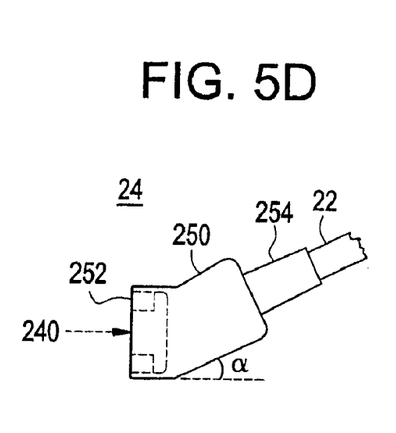

FIGS. 5(a) through 5(d) show the configuration of the connector 24 from four directions. FIG. 5(a) is a front elevational view, FIG. 5(b) is a top plan view, FIG. 5(c) is a rear view, and FIG. 5(d) is a lateral side view. As shown, the connector 24 has a connector case 250 containing an electric contact assembly 240 therein. The connector case 250 has an opening 252 in its front. The electric contact assembly 240 protrudes toward the opening 252 within the connector case 250.

The connector case 250 is an embodiment of the connector case of the present invention. The configuration of the case represents an embodiment of the connector case in accordance with the present invention. The connector case 250 is also an embodiment of the connector case in the ultrasonic probe and the ultrasonic imaging apparatus of the present invention. The electric contact assembly 240 is an embodiment of the electric contact assembly of the present invention.

The electric contact assembly 240 has a plurality of pin-like electric contacts 242. The electric contact number assignment is represented in the drawing by that at a single location. The plurality of electric contacts 242 are implanted on a substrate (not shown) in parallel with one another toward the front. The plurality of electric contacts 242 are surrounded by a sleeve 244. The length of the sleeve 244 is slightly larger than the length of the electric contacts 242.

The cable 22 is led out of the rear surface of the connector case 250 through a cylindrical portion 254. A plurality of electric wires constituting the cable 22 are connected to respective ones of the electric contacts 242 within the connector case 250.

The lower surface of the rear portion of the connector case 250 forms an elevation angle α with respect to a direction extended from the lowest surface, or the bottom surface, of the connector case 250. Accordingly, the cylindrical portion 254 and the cable led out of the portion 254 also have the same elevation angle α. Although the upper surface of the rear portion is shown to have the same elevation angle in FIG. 5, the upper surface need not have such an elevation angle, and it suffices for at least the lower surface to have the elevation angle α. The connector 24 thus constructed is inserted into the receptacle 500 in the imaging apparatus body 100.

Figure 6:
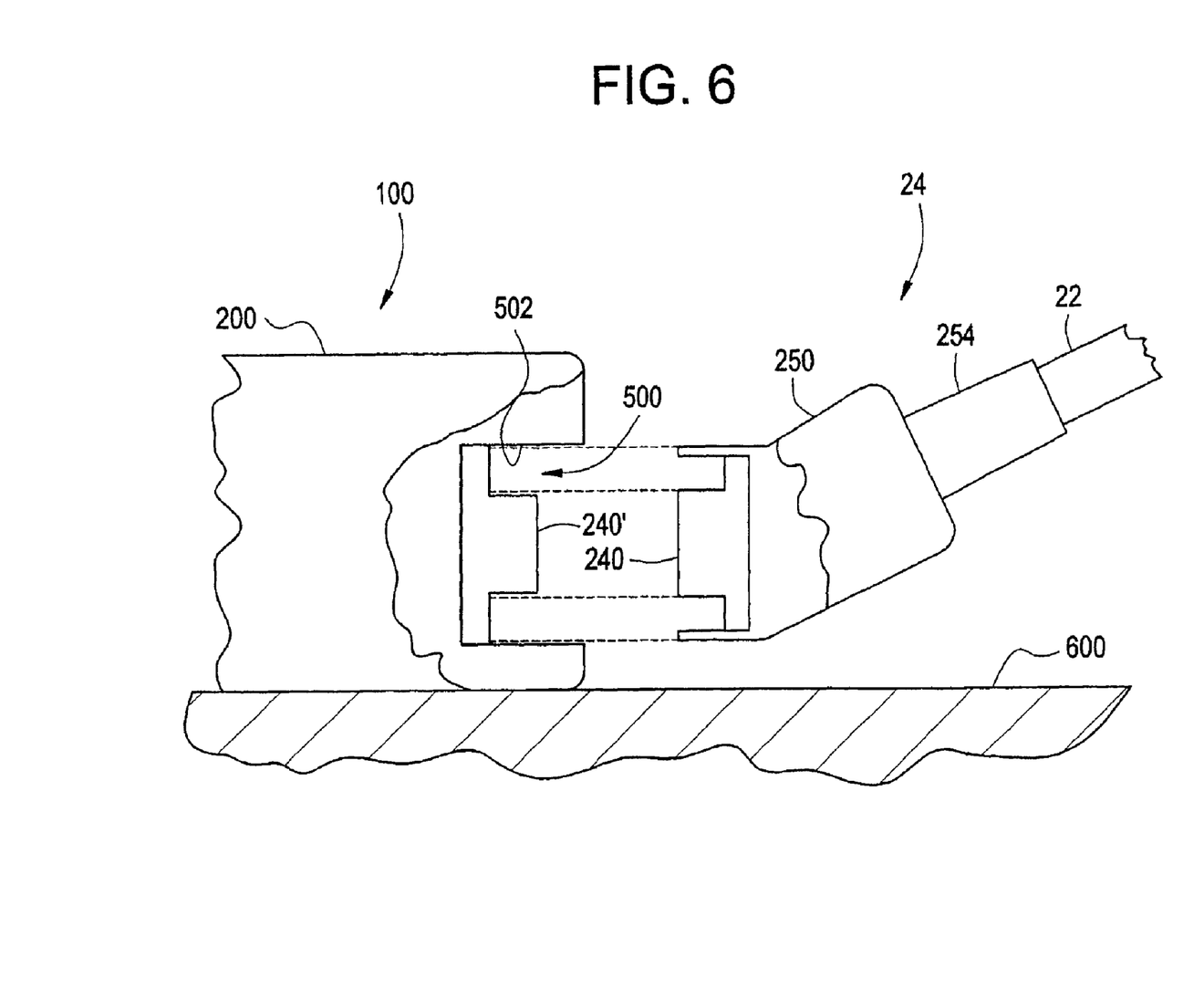
FIG. 6 is a schematic view showing the relationship between the connector and a receptacle.

FIG. 6 shows the relationship between the connector 24 and the receptacle 500. As shown, the receptacle 500 is comprised of a concave portion having an opening 502 into which the front portion of the connector 24 can be inserted, and an electric contact assembly 240'. The electric contact assembly 240' is provided inside the concave portion. The electric contact assembly 240' protrudes toward the opening 502 of the receptacle 500.

The electric contact assembly 240' is a contact counterpart for the electric contact assembly 240 of the connector 24. The outer periphery of the electric contact assembly 240' has a shape and size matched to the inner dimension of the sleeve 244 of the electric contact assembly 240, and also has a plurality of holes (not shown) matched to the plurality of electric contacts (pins) 242 in the electric contact assembly 240. Each hole has an electric contact strip on its inner surface. The electric contact strips are connected to an electric circuit within the imaging apparatus body 100. The electric contact assembly 240 and the electric contact assembly 240' are engaged with each other by inserting the connector 24 into the receptacle 500, thereby establishing electric connection.

Since the imaging apparatus body 100 is of slim type, the height of the lower side of the receptacle 500 from a supporting surface 600 on which the imaging apparatus body 100 is placed is quite small. However, the connector 24 has an elevation angle at the lower surface of the rear portion, and hence the clearance between the lower surface of the rear portion of the connector 24 and the supporting surface 600 is sufficiently large. Thus, insertion and withdrawal of the connector 24 by the user's hand can be easily done.

On the other hand, when the user attempts to insert the connector 24 into the receptacle 500 inversely with respect to the top-bottom direction of the connector 24, due to a mistake for example, the rear portion, the cylindrical portion 254 and the cable 22 exiting from the rear portion of the connector 24 interfere with the supporting surface 600 because the elevation angular configuration of the rear portion works inversely, Therefore, the insertion of the connector 24 is difficult, That is, correct insertion is easy to do and incorrect insertion is difficult to do, and thus correct connector insertion is spontaneously conducted.

Figure 7A:
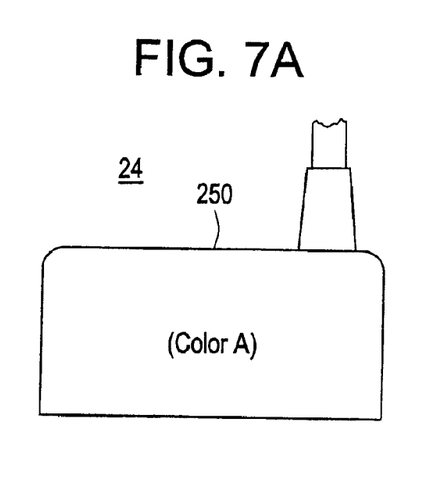
FIG. 7 is the configuration of the connector.
Figure 7B:
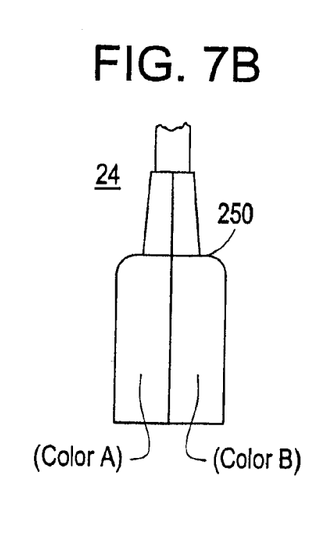
Figure 7C:
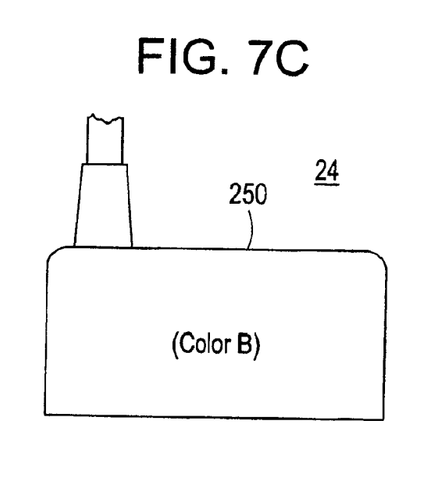

Correct connector insertion can be facilitated by utilizing the color of the connector instead of forming an elevation angle at the rear portion of the connector case as above. An example of such a case is shown in FIGS. 7(a) through 7(c). FIG. 7(a), FIG. 7(b) and FIG. 7(c) are top plan view, lateral side view and bottom plan view of the connector 24, respectively. As shown, the connector case 250 exhibits a color A on its upper half surface, or on a side that is obverse when the connector case 250 is correctly inserted into the receptacle 500; and exhibits a color B on its lower half surface, or on a side that is reverse when the connector case 250 is correctly inserted in the receptacle 500.

The colors A and B are different from each other: for example, the color A is a quiet or inconspicuous color, and the color B is a loud or conspicuous color. Thus, when the user attempts to insert the connector inversely by mistake, the conspicuous color B, for example, is perceived and the user becomes aware of the mistake easily. Such coloring may be combined with the formation of the elevation angle as described above.

Figure 8:
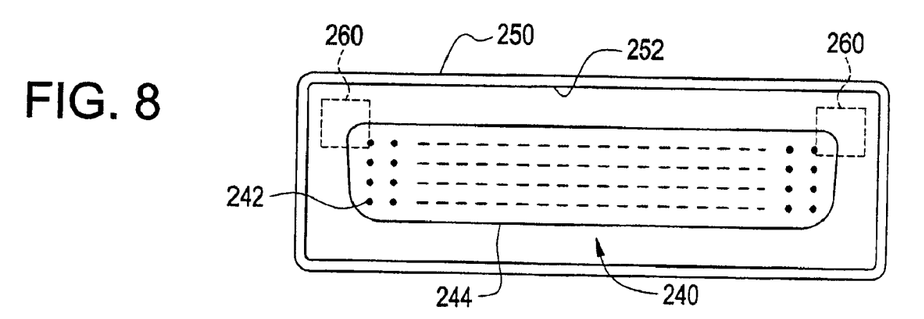
FIG. 8 is a front view of the connector.

The prevention of wrong connector insertion may also be achieved by mechanical stopping means. Specifically, as exemplarily shown in FIG. 8, an insertion stopping mechanism 260 is provided on either side of the upper portion of the sleeve 244 around the electric contact assembly 240 to stop the incorrect insertion.

Figure 9:
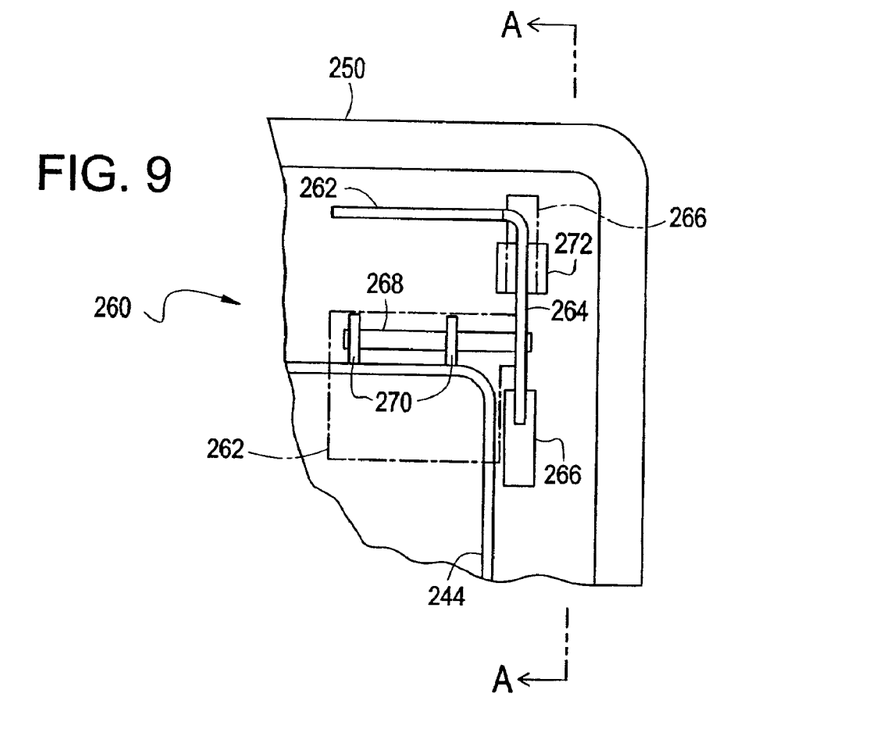
FIGS. 9 and 10 show the configuration of an insertion stopping mechanism.
Figure 10:
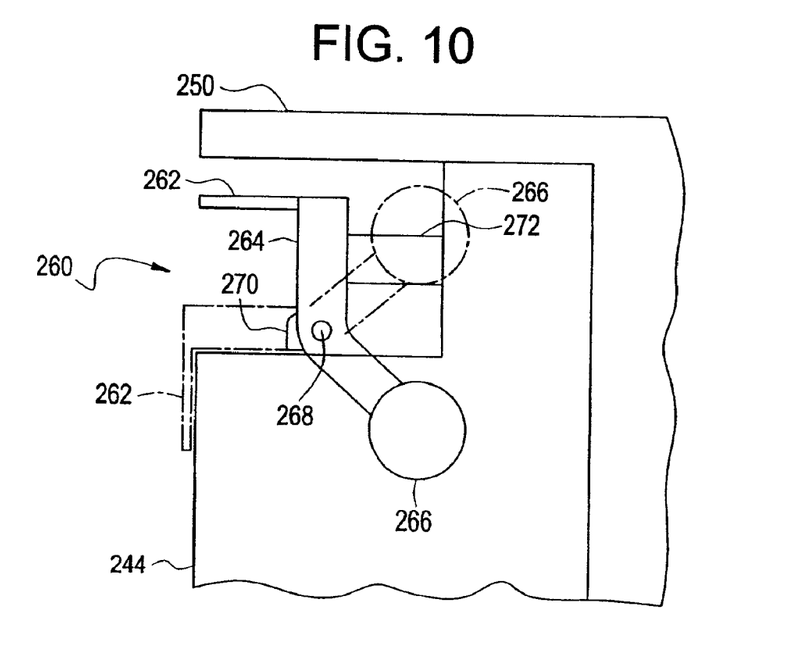

FIGS. 9 and 10 show enlarged views of a portion at which the insertion stopping mechanism 260 is disposed. A right end portion is illustrated in FIGS. 9 and 10. A left end portion is in symmetry with the right end portion. FIG. 9 is a front elevational view and FIG. 10 is a cross-sectional view across line A—A.

As shown, the insertion stopping mechanism 260 has a stem 268 rotatably supported by a bearing 270 provided on the outer periphery of the sleeve 244. The tip of the stem 268 is attached with an arm 264. The direction of the arm 264 is perpendicular to the stem 268. The arm 264 is elbowed in a plane perpendicular to the stem 268.

The arm 264 is provided with a stopper plate 262 and a weight 266 respectively at the ends. The stopper plate 262 is parallel to the stem 268. The stopper plate 262 is an embodiment of the insertion stopping member of the present invention. The stopper plate 262, arm 264 and weight 266 constitute a rotator that is rotatable around the stem 268. A portion from the stem 268 to the stopper plate 262 in the arm 264 will be sometimes referred to as an upper arm, and a portion from the stem 268 to the weight 266 as a lower arm hereinbelow.

The moment of rotations of the lower arm having the weight 266 is larger than that of the upper arm having the stopper plate 262. Accordingly, the rotator attempts to rotate to a position at which the lower arm stands vertically owing to gravity acting on the weight 266, but the rotation is inhibited by the upper arm colliding with a stopper 272. As a result, the rotator stops with the upper arm standing upright. In this condition, the stopper plate 262 lifts up away from the front surface of the sleeve 244. The position of the stopper plate 262 at this time will be sometimes referred to as a release position hereinbelow.

When the stopper plate 262 is in the release position, the connector 24 can be inserted into the receptacle 500 to engage the electric contact assembly 240 with the electric contact assembly 240' in the receptacle 500.

On the other hand, when the user attempts to insert the connector 24 into the receptacle 500 inversely with respect to the top-bottom direction of the connector 24, the top-bottom relationship is inverted with respect to that in FIGS. 9 and 10, and the arm 264 rotates counterclockwise in FIG. 10 owing to gravity acting on the weight 266 and stops at a position where the stopper plate 262 collides with the sleeve 244. The position of the stopper plate 262 at this time will be sometimes referred to as a stopping position.

In the stopping position, the stopper plate 262 overlaps the front surface of the sleeve 244, as indicated by broken line in FIGS. 9 and 10. Accordingly, even if the user attempts to insert the connector 24 to the receptacle 500, it is impossible to engage the electric contact assembly 240 with the electric contact assembly 240', thereby preventing the wrong insertion.

Such an insertion stopping mechanism may be provided in the connector which has the elevation angle or in that which is color-coded as described above. Thus, the prevention of wrong insertion can be achieved more securely.

The prevention of wrong insertion may moreover be performed by a warning generated as a noise or automatic voice message. For this purpose, the connector 24 and the receptacle 500 are configured as exemplarily shown in FIG. 11. As shown, a light-emitting element 504 and a light-receiving element 506 are provided inside the receptacle 500, and a reflector 508 is provided inside the connector 24.

Figure 11:
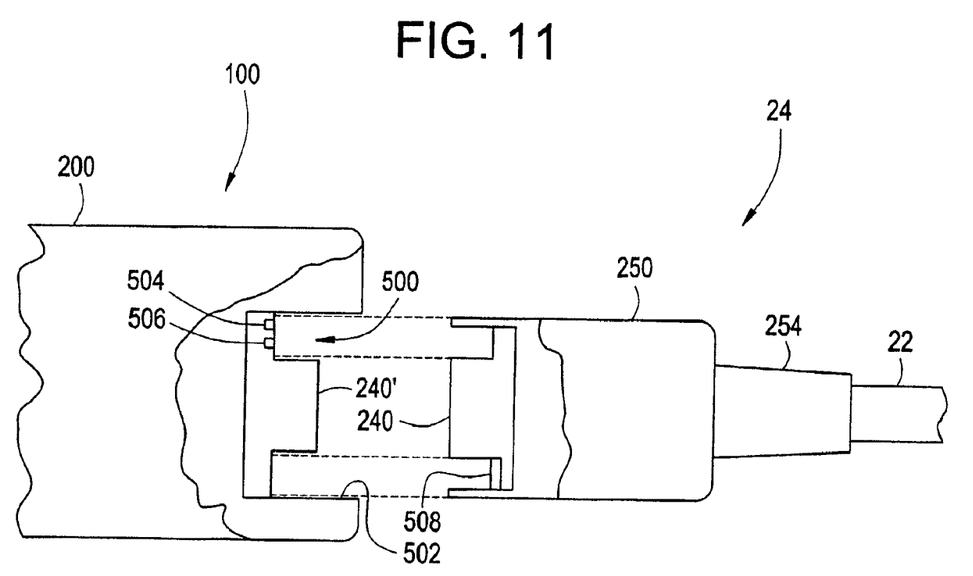
FIG. 11 is a schematic view showing the relationship between the connector and the receptacle.

The light emitting element 504 and light receiving element 506 are disposed in the upper portion of the innermost surface of the receptacle 500 so that they face toward the opening 502 of the receptacle 500. The reflector 508 is disposed in the lower portion of the innermost surface of the connector case 250.

By such a configuration, when the connector 24 is inserted into the receptacle 500 in a correct orientation, the light-emitting element 504 and reflector 508 do not face each other and the quantity of light received by the light-receiving element 506 is low; however, when the user attempts to insert the connector 24 inversely in the top-bottom direction, the light-emitting element 504 and reflector 508 face each other and the quantity of light received by the light-receiving element 506 is increased. Thus, correctness of the orientation in which the connector 24 is inserted can be determined from the quantity of light received by the light-receiving element 506.

Figure 12:
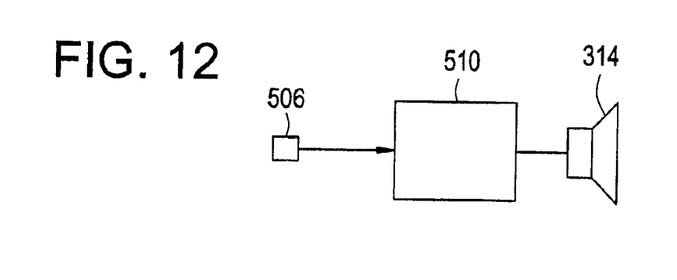
FIG. 12 is a block diagram of means of generating a warning of wrong insertion.

Thus, as shown in FIG. 12, a wrong insertion is detected based on the quantity of light received by the light-receiving element 506 at a warning unit 510 provided in the imaging apparatus body 100. When wrong insertion is detected, a warning generated as a noise or voice message is made through the sound output device 314. The voice message is desirably multilingual. A portion including the light-receiving element 506, warning unit 510 and voice output device 314 is an embodiment of the warning means of the present invention.

While the present invention has been described with reference to preferred embodiments hereinabove, various changes or substitutions may be made on these embodiments by those ordinarily skilled in the art pertinent to the present invention without departing from the technical scope of the present invention. Therefore, the technical scope of the present invention encompasses not only those embodiments described above but all the embodiments that fall within the scope of the appended claims.

Many widely different embodiments of the invention may be constructed without departing from the spirit and the scope of the present invention. It should be understood that the present invention is not limited to the specific embodiments described in the specification, except as defined in the appended claims.

What is claimed is:

1. A connector case comprising:
    a front portion to be inserted into a receptacle and a rear portion, opposite said front portion, out of which a cable is led;
    an electric contact assembly configured to be coupled to said receptacle; and
    a first surface that includes a first subsurface and a second subsurface forming an angle greater than zero with the first subsurface, and when said connector case is coupled to said receptacle, the second subsurface interferes with a third surface on which an imaging system including said receptacle is placed.

2. A connector case having a front portion to be inserted into a receptacle and a rear portion, opposite said front portion, out of which a cable is led, and containing an electric contact assembly, wherein said connector case has a first color on a first side that is obverse when the front portion can be inserted into the receptacle in a horizontal direction, wherein the first color is different from a second color on a second side of said connector case.

3. A connector case comprising:
    a front portion to be inserted into a receptacle and a rear portion, opposite said front portion, out of which a cable is led, wherein said receptacle includes a first electric contact assembly;
    a second electric contact assembly; and
    an insertion stopping member that moves from an insertion stopping position to a release position, wherein when said insertion stopping member is in the insertion stopping position, said insertion stopping member lies between said first and second contact assemblies.

4. The connector case as defined by claim 3, wherein said insertion stopping member includes a stopper plate that is provided with a pivotally supported arm having a weight at one end and said stopper plate at another end.

5. An ultrasonic probe comprising:
    a probe body;
    a cable having one end connected to said probe body; and
    a connector case including:
        a front portion to be inserted into a receptacle and a rear portion, opposite said front portion, out of which said cable is led;
        an electric contact assembly connected to another end of said cable;
        a first surface that includes a first subsurface and a second subsurface forming an angle greater than zero with the first subsurface, and when said connector case is coupled to said receptacle, the second subsurface interferes with a third surface on which an imaging system including said receptacle is placed.

6. An ultrasonic probe comprising: a probe body; a cable having one end connected to said probe body; an electric contact assembly connected to the other end of said cable; and a connector case having a front portion to be inserted into a receptacle and a rear portion, opposite said front portion, out of which said cable is led, and containing said electric contact assembly, said connector case having a first color on a first side that is obverse when the front portion can be inserted into the receptacle in a horizontal direction, wherein the first color is different from a second color on a second side of said connector case.

7. An ultrasonic probe comprising:
    a probe body;
    a cable having one end connected to said probe body; and
    a connector case including:
        a front portion to be inserted into a receptacle and a rear portion, opposite said front portion, out of which a cable is led, wherein said receptacle includes a first electric contact assembly;
        a second electric contact assembly connected to another end of said cable; and
        an insertion stopping member that moves from an insertion stopping position to a release position, wherein when said insertion stopping member is in the insertion stopping position, said insertion stopping member lies between said first and second contact assemblies.

8. The ultrasonic probe as defined by claim 7, wherein said insertion stopping member includes a stopper plate that is provided with a pivotally supported arm having a weight at one end and said stopper plate at another end.

9. An ultrasonic imaging apparatus comprising:
    an imaging apparatus body provided with a receptacle;
    a probe body;
    a cable having one end connected to said probe body; and
    a connector case including:
        a front portion to be inserted into said receptacle and a rear portion, opposite said front portion, out of which said cable is led;
        an electric contact assembly connected to another end of said cable;
        a first surface that includes a first subsurface and a second subsurface forming an angle greater than zero with the first subsurface, and when said connector case is coupled to said receptacle, the second subsurface interferes with a third surface on which an imaging system including said receptacle is placed.

10. The ultrasonic imaging apparatus as defined by claim 9, wherein said imaging apparatus body has a generally rectangular-parallelepiped outer shape, wherein said imaging apparatus body has a height dimension that is smaller than length and width dimensions, and said imaging apparatus body has a housing provided with said receptacle on a surface of said imaging apparatus body.

11. The ultrasonic imaging apparatus as defined by claim 10, wherein said imaging apparatus body has on an upper surface of said housing a generally planar display section that is tiltable around a hinge.

12. An ultrasonic imaging apparatus comprising: an imaging apparatus body provided with a receptacle; a probe body; a cable having one end connected to said probe body; an electric contact assembly connected to the other end of said cable; and a connector case having a front portion to be inserted into said receptacle and a rear portion, opposite said front portion, out of which said cable is led, and containing said electric contact assembly, said connector case having a first color on a first side that is obverse when the front portion can be inserted into the receptacle in a horizontal direction, wherein the first color is different from a second color on a second side of said connector case.

13. The ultrasonic imaging apparatus as defined by claim 12, wherein said imaging apparatus body has a generally rectangular-parallelepiped outer shape, wherein said imaging apparatus body has a height dimension that is smaller than length and width dimensions, and said imaging apparatus body has a housing provided with said receptacle on a surface of said imaging apparatus body.

14. An ultrasonic imaging apparatus comprising:
   an imaging apparatus body provided with a receptacle;
   a probe body;
   a cable having one end connected to said probe body; and
   a connector case including:
      a front portion to be inserted into a receptacle and a rear portion, opposite said front portion, out of which a cable is led, wherein said receptacle includes a first electric contact assembly;
      a second electric contact assembly connected to another end of said cable; and
      an insertion stopping member that moves from an insertion stopping position to a release position, wherein when said insertion stopping member is in the insertion stopping position, said insertion stopping member lies between said first and second contact assemblies.

15. The ultrasonic imaging apparatus as defined by claim 14, wherein said insertion stopping member includes a stopper plate that is provided with a pivotally supported arm having a weight at one end and said stopper plate at another end.

16. The ultrasonic imaging apparatus as defined by claim 14, wherein said imaging apparatus body has a generally rectangular-parallelepiped outer shape, wherein said imaging apparatus body has a height dimension that is smaller than length and width dimensions, and said imaging apparatus body has a housing provided with said receptacle on a surface of said imaging apparatus body.

17. An ultrasonic imaging apparatus comprising: an imaging apparatus body provided with a receptacle; a probe body; a cable having one end connected to said probe body; a connector case having a front portion to be inserted into said receptacle and a rear portion, opposite said front portion, out of which said cable is led, and containing an electric contact assembly connected to the other end of said cable therein; and warning means for generating a warning sound based on an orientation in which said connector case is inserted into said receptacle.

18. The ultrasonic imaging apparatus as defined by claim 17, wherein said sound is a noise.

19. The ultrasonic imaging apparatus as defined by claim 17, wherein said sound is a voice message.

20. The ultrasonic imaging apparatus as defined by claim 19, wherein said voice message is a multilingual voice message.

21. The ultrasonic imaging apparatus as defined by claim 17, wherein said imaging apparatus body has a generally rectangular-parallelepiped outer shape, wherein said imaging apparatus body has a height dimension that is smaller than length and width dimensions, and said imaging apparatus body has a housing provided with said receptacle on a surface of said imaging apparatus body.

* * * * *